(12) United States Patent
Stephens

(10) Patent No.: US 10,363,175 B2
(45) Date of Patent: Jul. 30, 2019

(54) CARTON WITH A RECLOSABLE OPENING

(71) Applicant: The Procter & Gamble Company, Cincinnati, OH (US)

(72) Inventor: Jerry Ray Stephens, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 200 days.

(21) Appl. No.: 14/755,628

(22) Filed: Jun. 30, 2015

(65) Prior Publication Data
US 2017/0000666 A1   Jan. 5, 2017

(51) Int. Cl.
*B65D 85/00* (2006.01)
*A61F 13/551* (2006.01)
*B65D 5/02* (2006.01)
*B65D 5/10* (2006.01)

(52) U.S. Cl.
CPC ...... *A61F 13/55145* (2013.01); *B65D 5/0227* (2013.01); *B65D 5/10* (2013.01)

(58) Field of Classification Search
CPC ............ A61F 13/55145; A61F 13/5513; A61F 15/001; A61F 13/55105; A61F 13/551; B65D 5/0227; B65D 5/66; B65D 5/0272; B65D 5/103; B65D 85/1036
USPC ............... 206/526, 271, 391, 396, 440, 390; 229/905, 234, 242, 124, 156, 160.2, 182.1
See application file for complete search history.

(56) References Cited

U.S. PATENT DOCUMENTS

| | | | |
|---|---|---|---|
| 1,606,439 A * | 11/1926 | Metzger | B65D 5/701 206/69 |
| 3,608,812 A | 9/1971 | Hamilton | |
| 3,893,614 A | 7/1975 | Meyers | |
| 3,971,506 A * | 7/1976 | Roenna | B65D 5/701 229/234 |
| 6,223,507 B1 | 5/2001 | Tisma | |
| 6,935,506 B1 | 8/2005 | Boyle et al. | |
| 8,752,708 B2 | 6/2014 | Keefe | |
| 2003/0085265 A1 | 5/2003 | Haim | |
| 2005/0109827 A1 | 5/2005 | Martin | |
| 2005/0178788 A1 | 8/2005 | Shannon et al. | |
| 2005/0199695 A1 | 9/2005 | Debusk et al. | |
| 2006/0016711 A1 * | 1/2006 | Ritter | B65D 73/0092 206/470 |
| 2006/0049067 A1 | 3/2006 | McDonald | |
| 2006/0049074 A1 | 3/2006 | Long et al. | |
| 2006/0131197 A1 * | 6/2006 | Price | A61F 15/001 206/440 |
| 2007/0095881 A1 | 5/2007 | Manaige | |
| 2007/0199979 A1 | 8/2007 | Holley | |
| 2008/0073420 A1 | 3/2008 | Walling et al. | |
| 2008/0135605 A1 | 6/2008 | Manaige | |

(Continued)

FOREIGN PATENT DOCUMENTS

| | | |
|---|---|---|
| GB | 2328201 A | 2/1999 |
| GB | 2342343 A | 4/2000 |
| WO | WO-2004/018308 A2 | 3/2004 |

*Primary Examiner* — Rafael A Ortiz
(74) *Attorney, Agent, or Firm* — William E. Gallagher

(57) ABSTRACT

A reclosable carton being capable and being adapted for accommodating a multiplicity of disposable absorbent articles is provided. The reclosable carton has a substantially parallelepiped-shape. A blank having a substantially folded flat-shape able to be converted in the reclosable carton is also provided.

3 Claims, 9 Drawing Sheets

(56) References Cited

U.S. PATENT DOCUMENTS

| | | |
|---|---|---|
| 2009/0072015 A1 | 3/2009 | Drew et al. |
| 2010/0006458 A1 | 1/2010 | Wilkins et al. |
| 2010/0084308 A1 | 4/2010 | Rigby |
| 2010/0108550 A1 | 5/2010 | Cesare et al. |
| 2010/0122998 A1 | 5/2010 | Burke |
| 2011/0204130 A1 | 8/2011 | McLeod |
| 2012/0160905 A1 | 6/2012 | Wilkum et al. |
| 2012/0199640 A1 | 8/2012 | Thorne et al. |
| 2012/0292382 A1 | 11/2012 | Cai et al. |
| 2013/0203575 A1 | 8/2013 | Ross |
| 2013/0319886 A1 | 12/2013 | Ledermann |
| 2014/0234505 A1 | 8/2014 | Burke |

\* cited by examiner

CARTON WITH A RECLOSABLE OPENING

FIELD OF THE INVENTION

The present invention relates to a reclosable carton capable of receiving and holding a multiplicity of disposable absorbent articles, such as tampons. More particularly, the present invention relates to a reclosable carton having a substantially parallelepiped-shape. The present invention refers to a carton that is easily opened and re-closed by a consumer.

The present invention also relates to a blank having a substantially flat-shape able to be converted in the reclosable carton having a substantially parallelepiped-shape.

BACKGROUND OF THE INVENTION

Reclosable cartons used in the food industry such as the cereal boxes generally comprise a front and rear wall opposite to the front wall, first and second opposite side wall, a top wall, and a bottom wall opposite to the top wall. Such cartons are typically provided with a closure device comprising a tab on a flap extending from an upper portion of one of the front or rear walls and a slot in a tap extending from the other of the front or rear walls. The tab is receivable in the slot to effect reclosure of the carton after being opened, see for example U.S. Patent Application US 2012/0160905 A1.

It might occur that the consumers dislike having to open multiple flaps to get access to the articles stored in the carton. Hence, a need still exists to provide a carton with an easy and intuitive opening and easily and reliably reclosable while keeping the articles safe from any kind of contamination.

SUMMARY OF THE INVENTION

A reclosable carton for accommodating a plurality of disposable absorbent articles, having a substantially parallelepiped-shape is provided and comprises a front wall, a rear wall opposite to the front wall, a first and second opposite side walls, a top wall, a bottom wall opposite to the top wall and a lid. The lid is continuous with the rear wall along a hinge line and is overlaying the top wall. The lid has first and second opposite transversal edges and first and second opposite longitudinal edges. The first transversal edge of the lid coincides with the hinge line. At least a portion of the second transversal edge of the lid is a curve.

The top wall comprises first and second opposite transversal edges and first and second opposite longitudinal edges. The first transversal edge of the top wall is substantially parallel to the hinge line. The top wall comprises first, second and third lines of weakness. The first and second lines of weakness extend, preferably perpendicularly, from the first transversal edge of the top wall. The third line of weakness converges with the first and second lines of weakness. The first line of weakness extends transversally inboard from the first longitudinal edge of the top wall. The second line of weakness extends transversally inboard from the second longitudinal edge of the top wall. The third line of weakness extends longitudinally inboard from the second transversal edge of the top wall.

At least a portion of the third line of weakness of the top wall is a curve. The curve of the third line of weakness extends from a first location to a second location of the third line of weakness. The curve of the second transversal edge of the lid and the curve of the third line of weakness of the top wall are offset with each other at least between the first and second location of the third line of weakness by an offset distance. The offset distance between the curve of the second transversal edge of the lid and the curve of the third line of weakness of the top wall varies and reaches a maximum value between the first and second location of the third line of weakness. The second transversal edge of the lid is able to slip below the third line of weakness of the top wall such that the carton is reclosable.

A blank having a substantially flat-shape able to be converted into a reclosable carton for accommodating a plurality of disposable absorbent articles, the reclosable carton having a substantially parallelepiped-shape, is also provided and comprises a front wall, a rear wall, a first and second opposite side walls, a top wall, a bottom wall opposite to the top wall and a lid. The bottom wall is foldably connected to the rear wall at a fold line of the bottom wall. The lid is foldably connected to the rear wall at a fold line of the lid, wherein the lid is opposite to the bottom wall.

The front wall is opposite to the rear wall and is foldably connected to the bottom wall at a fold line of the front wall. The fold line of the front wall is parallel to the fold line of the bottom wall. The first side wall is foldably connected to the front wall at a fold line of the first side wall. The second side wall is opposite to the first side wall and is foldably connected to the front wall at a fold line of the second side wall. The fold line of the first side wall is parallel to the fold line of the second side wall. The top wall is foldably connected to the front wall at a fold line of the top wall. The fold line of the top wall is parallel to the fold line of the front wall and perpendicular to the fold lines of the respective first and second side walls.

The lid has first and second opposite transversal edges and first and second opposite longitudinal edges. The first transversal edge of the lid coincides with the fold line of the lid. The fold line of the lid connects the lid to the rear wall. At least a portion of the second transversal edge of the lid is a curve. The top wall comprises first and second opposite transversal edges and first and second opposite longitudinal edges. The first transversal edge of the top wall is substantially parallel to the fold line of the top wall. The top wall comprises first, second and third lines of weakness. The first and second lines of weakness extend, preferably perpendicularly, from the first transversal edge of the top wall. The third line of weakness converges with the first and second lines of weakness. The first line of weakness extends transversally inboard from the first longitudinal edge of the top wall. The second line of weakness extends transversally inboard from the second longitudinal edge of the top wall. The third line of weakness extends longitudinally inboard from the second transversal edge of the top wall.

At least a portion of the third line of weakness of the top wall is a curve. The curve of the third line of weakness extends from a first location to a second location of the third line of weakness. When the blank is converted into the reclosable carton, the curve of the second transversal edge of the lid and the curve of the third line of weakness of the top wall are offset with each other at least between the first and second locations of the third line of weakness by an offset distance. The offset distance between the curve of the second transversal edge of the lid and the curve of the third line of weakness of the top wall varies and reaches a maximum between the first and second location of the third line of weakness. The second transversal edge of the lid is able to slip below the third line of weakness of the top wall such that the carton is reclosable.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definition of Terms

Figure 1:
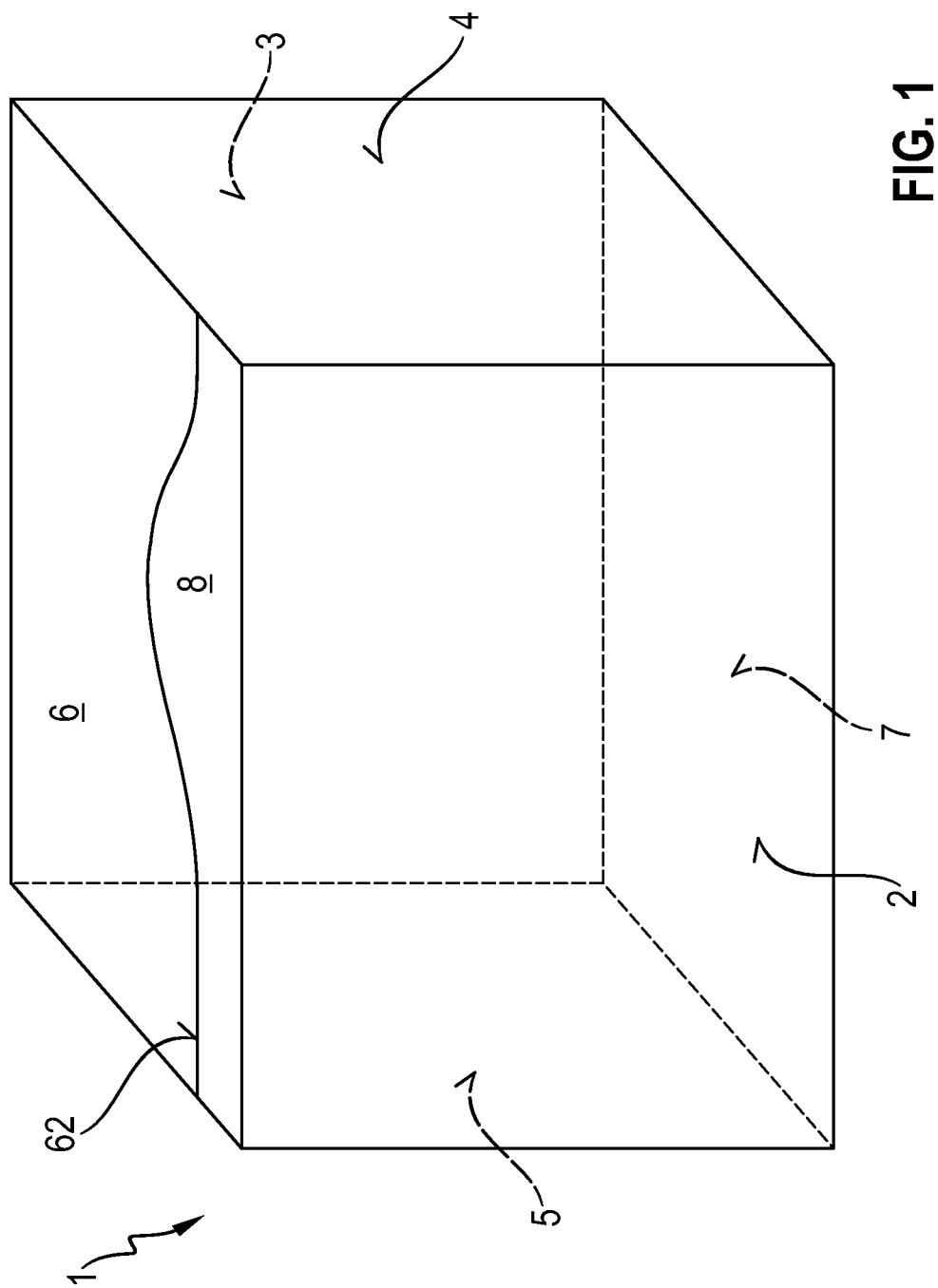
FIG. 1 is a schematic perspective view of a reclosable carton within the scope of the invention.

The term "absorbent article" as used herein refers to devices which absorb and contain body exudates, and, more specifically, refers to devices which are placed against or in proximity to the body of the wearer to absorb and contain the various exudates discharged from the body. Typical absorbent articles of the present invention include but are not limited to diapers, adult incontinence briefs, training pants, diaper holders and liners, absorbent inserts and the like, as well as feminine hygiene products, such as sanitary napkins and panty liners, tampons and the like. Absorbent articles also include wipes, such as household cleaning wipes, baby wipes, tissue towels and the like.

The term "disposable" as used herein refers to absorbent articles which generally are not intended to be laundered or otherwise restored or reused (i.e., they are intended to be discarded after a single use and, preferably, to be recycled, composted or otherwise discarded in an environmentally compatible manner).

"Comprise", "comprising", and "comprises" as used herein are open ended terms, each specifying the presence of what follows, e.g., a component, but not precluding the presence of other features, e.g., elements, steps or components known in the art, or disclosed herein.

The term "carton" as used herein refers to a paperboard or cardboard container, or a board made of a rigid plastic material having, in combination, (and distinguishable), a top wall, a bottom wall opposite to the top wall, a first and, a front wall, and a rear wall opposite to the front wall that collectively enclose and protect an interior space that is usable for packing, storing, shipping, and/or merchandizing a particular product, e.g. disposable absorbent articles. For the reclosable carton disclosed herein, and for most cartons in general, a bottom wall is recognized as the side of the carton that is intuitively placed on a surface when the reclosable carton is to remain stationary and a top wall of the reclosable carton is the location of an opening/access to the reclosable carton. For purposes of the present invention, the opening to the carton is reclosable. The carton may be made of a paperboard, coated paperboard that is coated with a natural or synthetic waterproof or water resistant material such as polyethylene or other synthetic or natural polymers, wax, other suitable materials or blends thereof.

The term "blank" as used herein refers to a term of art in the packaging industry that refers to a flat board/sheet that is cut to a pattern that may be erected into a carton structure. A "blank" may be a flat piece of corrugated board (paperboard, cardboard) or a flat piece made of a rigid plastic material that has various cut lines and fold lines such that a machine (called a conversion machine or a carton erector) can build it into a three-dimensional carton. Such blanks may also be cut with perforated lines that may outline locations where the erected box can be opened at a future time. Perforated lines may allow removal of a flap or may define a tear strip to open a sealed carton.

As used herein the expressions "front", "rear", "longitudinal", "transversal", "top", "side", "bottom" and the like, when used to describe the reclosable carton, relate to a filled carton placed in a carrying position with the bottom wall facing downwards and the top wall facing upwards, such as e.g. shown in the Figures.

The Reclosable Carton in a Parallelepiped Shape

Figure 2:
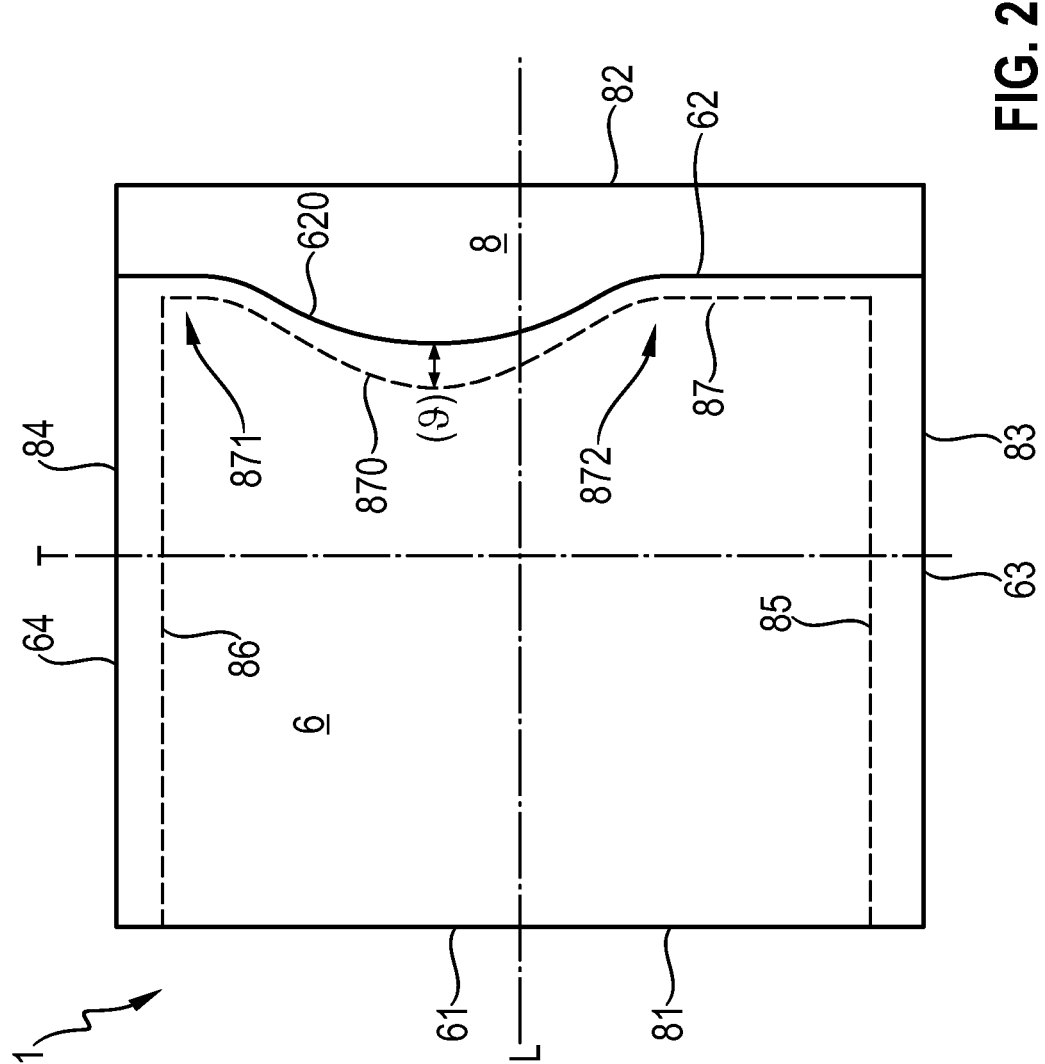
FIG. 2 is a top view of a reclosable carton before any opening.

FIG. 1 and FIG. 2 show a reclosable carton 1 within the scope of the invention. The reclosable carton 1 has a substantially parallelepiped-shape, i.e. a hexahedron shape.

The reclosable carton 1 can accommodate a plurality of disposable absorbent articles, such as from about 10 to about 100 or from about 10 to about 50 or from about 10 to about 20 disposable absorbent articles. For example, the reclosable carton 1 of the present invention may be used for accommodating a plurality of feminine hygiene articles, preferably tampons.

The reclosable carton 1 comprises a front wall 2, a rear wall 3 opposite to the front wall 2, a first and second opposite side wall 4, 5, a top wall 8, a bottom wall 7 opposite to the top wall 8 and a lid 6. The lid 6 is continuous with the rear wall 3 along a hinge line 61 (see FIG. 2). The lid 6 is overlaying the top wall 8.

FIG. 2 shows a top view of the reclosable carton 1 within the scope of the invention. The top wall 8 has a longitudinal axis L and a transversal axis T. The lid 6 has first and second opposite transversal edges 61, 62 and first and second opposite longitudinal edges 63, 64. The first transversal edge 61 of the lid 6 coincides with the hinge line 61. At least a portion of (or all of) the second transversal edge 62 of the lid 6 is a curve 620.

The top wall 8 comprises first and second opposite transversal edges 81, 82 and first and second opposite longitudinal edges 83, 84. The first transversal edge 81 of the top wall 8 is substantially parallel to the hinge line 61. Even, the first transversal edge 81 of the top wall 8 may coincide with the hinge line 61. The top wall 8 also comprises first, second and third lines of weakness 85, 86, 87. The first and second lines of weakness 85, 86 extend, preferably perpendicularly, from the first transversal edge 81 of the top wall 8. The third line of weakness 87 converges with the first and second lines of weakness 85, 86 such that a continuous line of weakness, comprising the first, second and third lines of weakness 85, 86, 87, is formed. The first line of weakness 85 extends transversally inboard from the first longitudinal edge 83 of the top wall 8. The second line of weakness 86 extends transversally inboard from the second longitudinal edge 84 of the top wall 8. The third line of weakness 87 extends longitudinally inboard from the second transversal edge 82 of the top wall 8.

Each of the first, second and third lines of weakness 85, 86, 87 may be continuous and/or intermittent. Each of the first, second and third lines of weakness 85, 86, 87 may be preferably perforated lines. Perforated lines may be small notches, small cuts, or holes, or combinations thereof. Each of the first, second and third lines of weakness 85, 86, 87 may be pierced or cut through one side or both sides of the corrugated board constituting the top wall 8.

At least a portion of (or all of) the third line of weakness 87 of the top wall 8 is a curve 870. The third line of weakness has a length and the portion of the third line of weakness 87 comprising a curve has a length. The length of the portion of the third line of weakness 87 comprising a curve may be from about ¼ to about ⅔ or from about ¼ to about ⅓ of the length of third line of weakness 87. The curve 870 of the third line of weakness 87 extends from a first location 871 to a second location 872 of the third line of weakness 87.

Known boxes, e.g. cereal box generally comprise a conventional arrangement of four flaps at a top of the box. The closure of the cereal box is essentially achieved by first pulling down two opposite flaps and then connecting the two remaining flaps together by inserting a tab of one of the two remaining flaps into a slot of the other opposite flap. Some consumers may find unpleasant to manipulate more than two flaps at the top of a carton to open it and to get access to its content.

Figure 3:
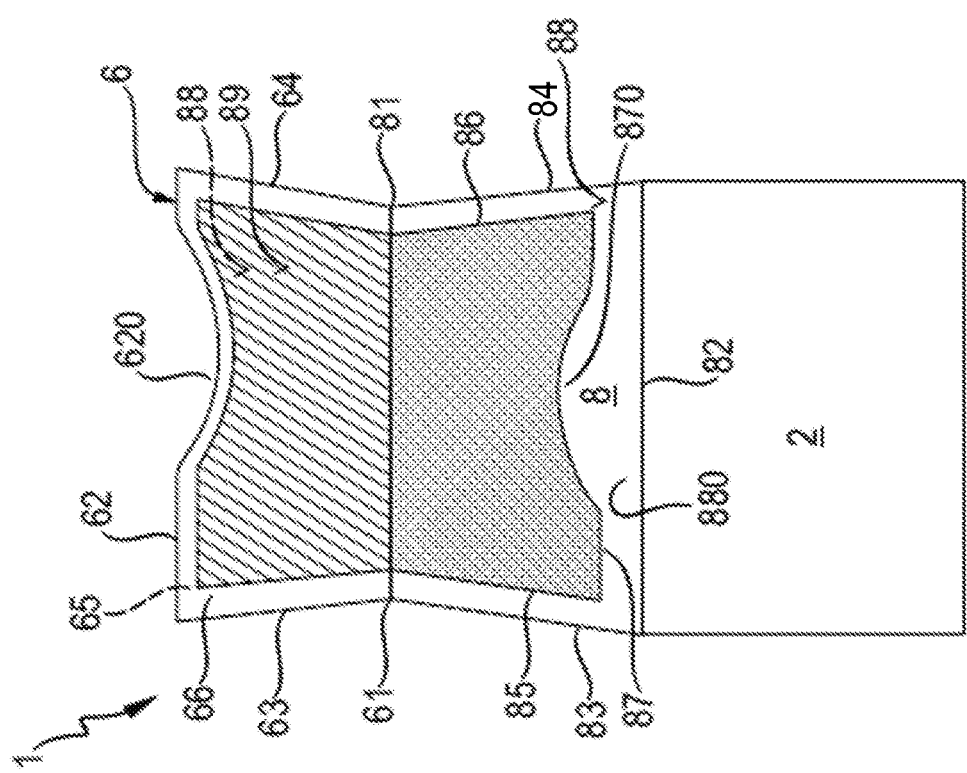
FIG. 3 is a schematic perspective view of the carton of FIG. 1 when it has been opened along the first, second and third lines of weakness of the top wall.

FIG. 3 is a schematic perspective view of the reclosable carton 1 when it has been opened along the first, second and third lines of weakness 85, 86, 87 of the top wall 8.

The lid 6 comprises upper and lower surfaces 65, 66. The top wall 8 comprises upper and lower surfaces 88, 89 as illustrated in FIG. 3.

The consumer can open the reclosable carton 1 by only grasping the lid 6 and detach a portion of the top wall 8 delimiting by the first, second and third lines of weakness 85, 86, 87. The portion of the top wall 8 delimited by the first, second and third lines of weakness 85, 86, 87 may be even removed after having been opened along the first, second and third lines of weakness 85, 86, 87. Indeed, the first transversal edge 81 of the top wall 8 is not connected to the hinge line 61 of the lid 6 and also not connected to any other walls.

Alternatively, as shown in FIG. 3, the upper surface 88 of the top wall 8 may be attached to the lower surface 66 of the lid 6 in an area that extends transversally inboard from the first and second line of weakness 85, 86 and that extends longitudinally inboard from the first transversal edge 81 and the third line of weakness 87 of the top wall 8.

The upper surface 88 of the top wall 8 may be attached to the lower surface 66 of the lid 6 with a uniform continuous layer of adhesive, a patterned layer of adhesive, or an array of separate lines, spirals, or spots of adhesive.

When the consumer opens the reclosable carton 1 only by grasping the lid 6, the upper surface 88 of the top wall 8 at the above defined area can remain permanently attached to the lower surface 66 of the lid 6, as shown in FIG. 3. Hence, the hinging lid 6 attached to the top wall 8 of the reclosable carton 1 provides a relatively easy opening for the consumer. The consumer does not need to manipulate more than one flap to open the reclosable carton 1.

Once opened, the top wall 8 comprises a frame 880 which is delimited by the first and second longitudinal edges 83, 84, portions of the remaining first transversal edge 81 of the top wall 8, the second transversal edge 82, and the first, second and third lines of weakness 85, 86, 87 of the top wall 8. In other words, the frame 880 is an area that extends transversally outboard from the first and second line of weakness 85, 86 and that extends longitudinally outboard from the first transversal edge 81 and the third line of weakness 87 of the top wall 8.

The frame 880 can help to improve the stability of the reclosable carton 1 by stiffening the top wall 8. When the carton 1 is opened, the frame 880 can stabilize the overall structure of the carton 1 by preventing any deformations of the front, rear and first and second side walls. The frame 880 of the top wall 8 can also provide a convenient access to the articles for the consumers when they want to grasp one or more articles. The frame 880 of the top wall 8 can be a location for providing some information for the consumers about the nature of the products, the usage instructions, or any warning information. Furthermore, the frame 880 of the top wall 8 can help to prevent any risk of contamination for the articles when the carton is closed or reclosed. Indeed, the frame 880 especially the areas of the frame 880 extending transversally inboard from the first and second longitudinal edges 83, 84 of top wall 8 prevents the exposure of the articles to the surrounding environment. When the carton 1 is reclosed, the articles are even not visible to the consumers due the frame 880.

Furthermore, as shown in FIG. 2, the lid 6 of the reclosable carton 1 overlays the top wall 8. The lid 6 may extend beyond the third line of weakness 87 of the top wall 8 towards the second transversal edge 82 of the top wall 8.

The lid 6 may extend beyond the first and second lines of weakness 85, 86 of the top wall 8 towards the respective first and second longitudinal edges 83, 84 of the top wall 8.

In that case, the frame 880 of the top wall 8 may have a reduced area such that the opening through the top wall 8 can be maximized. It may indeed be beneficial to vary the size of the frame 880 of the top wall 8 in order to adjust the size of the opening according to the size of the articles stored in the reclosable carton 1.

When the carton 1 is closed, as shown in FIG. 2, the curve 620 of second transversal edge 62 of the lid 6 and the curve 870 of the third line of weakness 870 of the top wall 8 are offset with each other at least between the first and second location 871, 872 of the third line of weakness 87 by an offset distance $\theta$. The offset distance $\theta$ between the curve 620 of the second transversal edge 62 of the lid 6 and the curve 870 of the third line of weakness 87 of the top wall 8 varies and reaches a maximum between the first and second location 871, 872 of the third line of weakness 87.

The offset distance $\theta$ between the curve 620 of the second transversal edge 62 of the lid 6 and the curve 870 of the third line of weakness 87 of the top wall 8 may vary from about 2% to about 30% or from about 4% to about 25% or from about 10% to about 25% of the first longitudinal edge 83 of the top wall 8.

The offset distance $\theta$ between the curve 620 of the second transversal edge 62 of the lid 6 and the curve 870 of the third line of weakness 87 of the top wall 8 may vary from about 3 mm to about 50 mm, or from about 3 mm to about 20 mm or from about 3 mm to about 10 mm, for all types of reclosable cartons.

The offset distance $\theta$ between the curve 620 of the second transversal edge 62 of the lid 6 and the curve 870 of the third line of weakness 87 of the top wall 8 may vary from about 3 mm to about 10 mm or from about 3 mm to about 5 mm for relative small sized reclosable cartons. A small sized reclosable carton may have a length/width/height of from about 5 cm to about 15 cm×from about 5 cm to about 15 cm×from about 5 cm to about 20 cm, for example.

The offset distance θ between the curve 620 of the second transversal edge 62 of the lid 6 and the curve 870 of the third line of weakness 87 of the top wall 8 may vary from about 5 mm to about 50 mm or from about 5 mm to about 30 mm or from about 10 mm to about 20 mm for medium sized reclosable cartons. A medium sized reclosable carton may have a length/width/height of from about 16 cm to about 70 cm×from about 16 cm to about 50 cm×from about 21 cm to about 70 cm, for example.

The maximum value of the offset distance may be from about 3 to about 50 mm or from about 3 mm to about 20 mm or from about 3 mm to about 5 mm, for all types of reclosable cartons.

The maximum value of the offset distance may be from about 3 to about 10 mm or from about 3.5 mm to about 5 mm for a small sized reclosable carton. The maximum value of the offset distance may be from about 5 mm to about 50 mm or from about 10 mm to about 20 mm for a medium sized reclosable carton.

The maximum value of the offset distance is chosen inter alia according to the stiffness of the material constituting the reclosable carton 1. A relatively high value for the maximum distance of the offset distance may be chosen if the paperboard or cardboard constituting the carton 1 has a relatively low stiffness. In that case, a relatively high value for the maximum distance of the offset distance can help to prevent any risk of deflection of the top wall 8 having a relatively low stiffness.

The second transversal edge 62 of the lid 6 is able to slip below the third line of weakness 87 of the top wall 8 such that the carton 1 is reclosable. Because the curve 620 of second transversal edge 62 of the lid 6 is offset from the curve 870 of the third line of weakness 870 of the top wall 8, the consumer can reclose the carton 1 by slipping the curved portion of the second transversal edge 62 of the lid 6 below the opened top wall 8. For this, the consumer only needs to push the upper surface 65 of the lid 6 downwards the top wall 8.

Compared to a typical cereal box opening, where the consumer may require two hands to align the tab and the slot of two respective opposite flaps to reclose the cereal box, the present carton 1 provides an easier, one-handed reclosure by only pushing the lid 6 on the top wall 8 until the closure is engaged. The reclosable carton 1 allows the consumer opening the lid 6, removing a disposable absorbent article, and reclosing conveniently the carton 1 with just one hand, even with only one finger.

Figure 4:
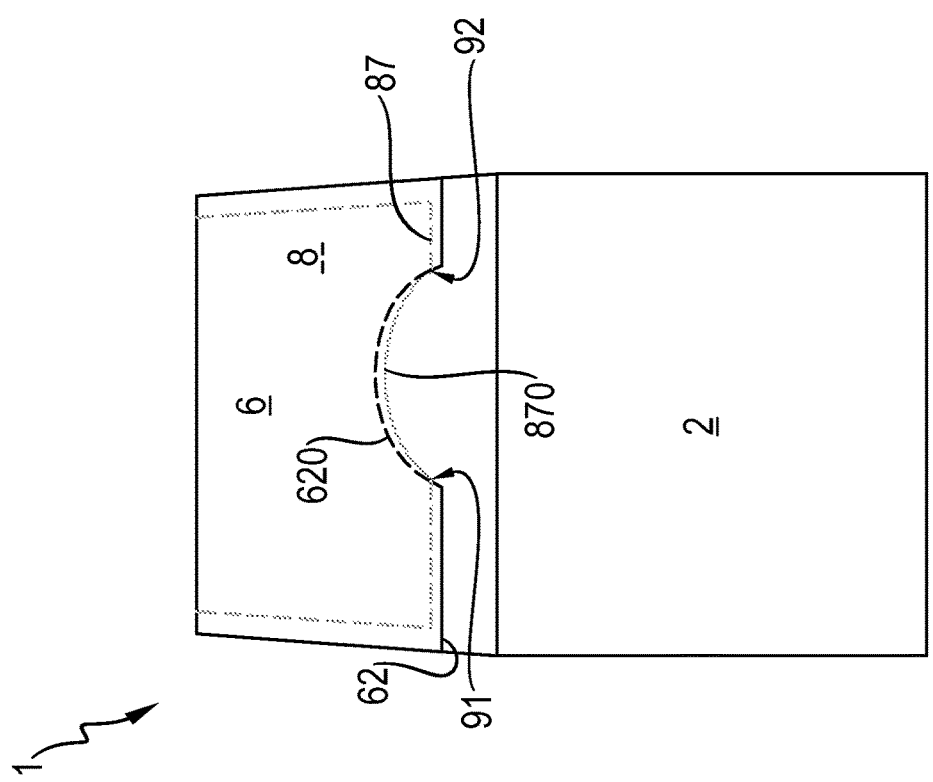
FIG. 4 is a schematic perspective view of the carton of FIG. 3 when the carton has been reclosed by slipping the second transversal edge of the lid below the third line of weakness of the top wall.

FIG. 4 is a schematic perspective view of the carton of FIG. 3 when the carton has been reclosed by slipping the curved portion of the second transversal edge 62 of the lid 6 below the curved portion of the third line of weakness 87 of the top wall 8. Particularly, the carton 1 may be reclosed by positioning the curve 620 of the second transversal edge 62 of the lid 6 below the curve 870 of the third line of weakness 87 of the top wall 8. The curve 620 of the second transversal edge 62 of the lid 6 and the curve 870 of the third line of weakness 87 of the top wall 8 may intersect at a first and second points of intersection 91, 92. In that case, the lid 6 slips below the top wall 8 to lead to a closure. Having the curve 620 of the second transversal edge 62 of the lid 6 offset to the curve 870 of the third line of weakness 87 of the top wall 8 provides a reliable closure engagement. A first and second points of intersection points 91, 92 can help the consumers to prevent any risk of contamination for the articles stored inside the carton 1.

Figure 5:
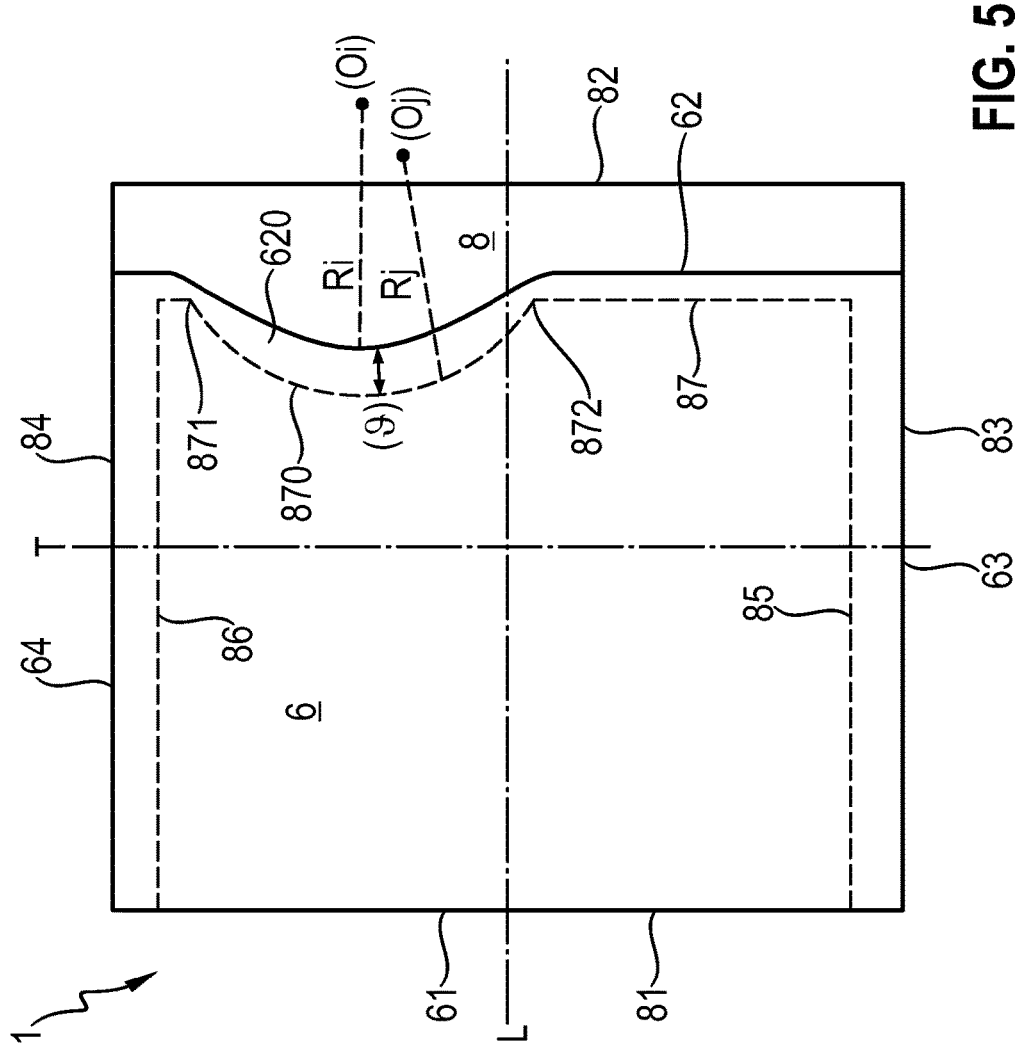
FIG. 5 is a top view of a reclosable carton before any opening according to another aspect of the present invention.

Advantageously, as exemplarily illustrated in FIG. 5, the curve 620 of the second transversal edge 62 of the lid 6 may be a portion of a first notional circle having a first radius Ri and a first center Oi. The curve 870 of the third line of weakness 87 of the top wall 8 may be a portion of a second notional circle having a second radius Rj and a second center Oj. The ratio between the first radius Ri of the curve 620 of the second transversal edge 62 of the lid 6 and the second radius Rj of the curve 870 of the third line of weakness 87 of the top wall 8 may be from about 1.3 to about 5 or from about 1.4 to about 3 or from about 1.5 to about 2.5.

The distance between the first and second centers Oi, Oj of the respective first and second notional circles may be from about 0 mm to about 50 mm or from about 3 to about 20 mm or from about 5 mm to about 10 mm.

The offset distance θ and the ratio between the first and second radius Ri, Rj of the respective the curve 620 of the second transversal edge 62 of the lid 6 and the curve 870 of the third line of weakness 87 of the top wall 8 can help to improve the reclosure of the carton 1 by creating well defined first and second points of intersection 91, 92, i.e. engagement points when the lid 6 is reclosed, i.e. when the curved portion of the lid 6 slips below the curved portion of the top wall 8. In that case, such improved reclosure of the carton 1 renders the articles stored inside the carton 1 less visible to the consumers.

The curve 620 of the second transversal edge 62 of the lid 6 and the curve 870 of the third line of weakness 87 of the top wall 8 may be both concave or both convex with respect to the hinge line 61.

Figure 6:
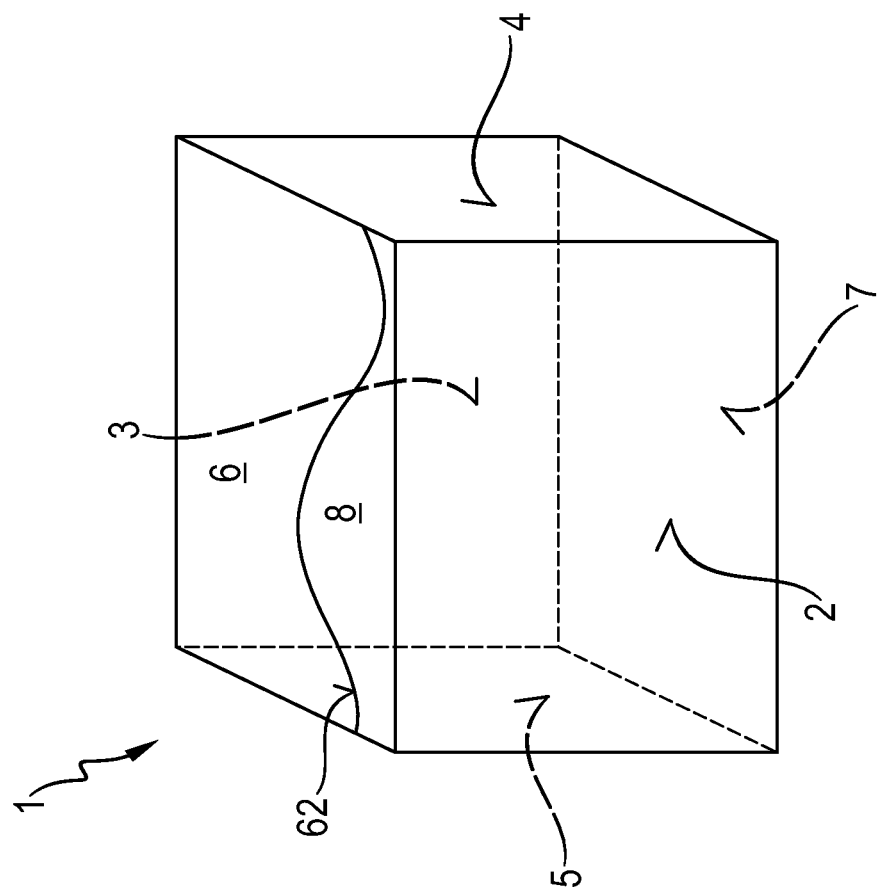
FIG. 6 is a schematic perspective view of another reclosable carton within the scope of the invention.
Figure 7B:
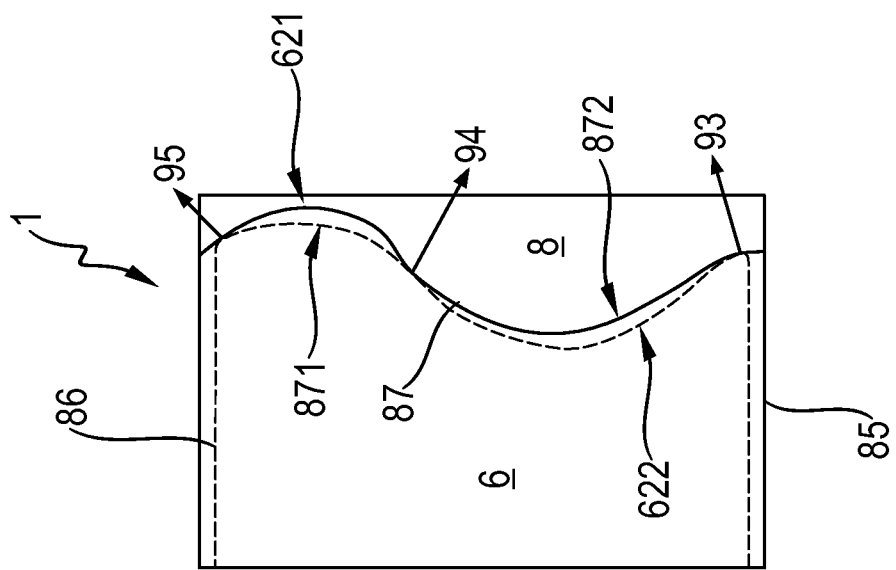
FIG. 7B is a top view of the reclosable carton of FIG. 7A when the carton has been reclosed.
Figure 7A:
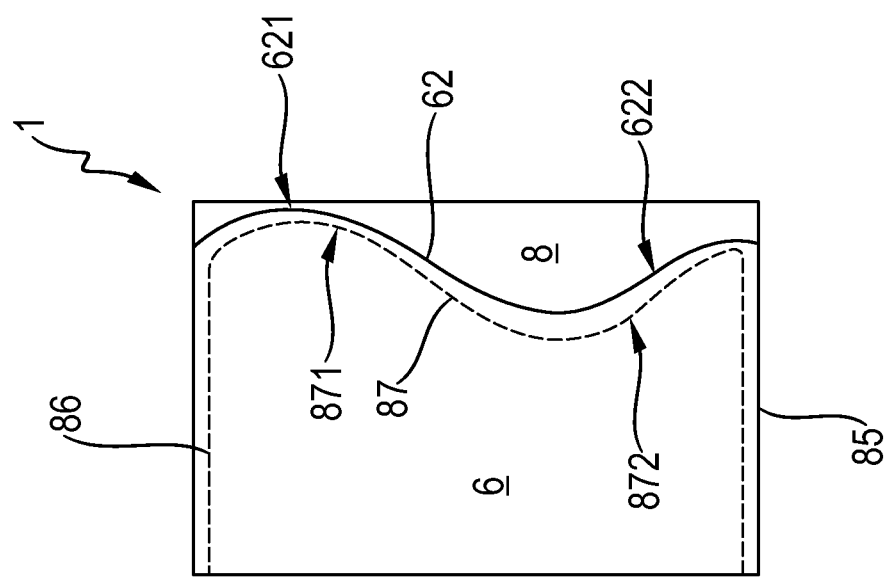
FIG. 7A is a top view of the reclosable carton of FIG. 6.

As shown in FIGS. 6 and 7A, the second transversal edge 62 of the lid 6 may comprise a first portion comprising a convex curve 621 and a second portion comprising a concave curve 622. The third line of weakness 87 of the top wall 8 may comprise a first portion comprising a convex curve 871 and a second portion comprising a concave curve 872 such that the convex curve 621 of the first portion the second transversal edge 62 of the lid 6 is offset with the convex curve 871 of the first portion of the third line of weakness 87 of the top wall 8 and the concave curve 622 of the second portion of the second transversal edge 62 of the lid 6 is offset with the concave curve 872 of the second portion of the third line of weakness 87 of the top wall 8.

Hence, the second transversal edge 62 of the lid 6 may be offset to the third line of weakness 87 of the top wall 8 and the offset distance between the second transversal edge 62 of the lid 6 and the third line of weakness 87 of the top wall 8 may vary from 3 mm to 50 mm or from 5 mm to 30 mm or from 5 mm to 20 mm. The convex curve 621 of the first portion of the second transversal edge 62 of the lid 6, for instance, can help the consumer grasp the lid 6 to open the reclosable carton 1 but also to reclose it.

When the carton 1 is reclosed, by slipping the first portion comprising a convex curve 621 of the second transversal edge 62 of the lid 6 below the first portion comprising a convex curve 871 of third line of weakness 87 of the top wall 8, and also the second portion comprising a concave curve 622 of the second transversal edge 62 of the lid 6 below the second portion comprising a concave curve 872 of third line of weakness 87 of the top wall 8, a reliable closure is obtained and is defined by at least three or more points of engagements 93, 94 and 95 (see FIG. 7B).

The Blank in a Flat-Shape

Figure 8:
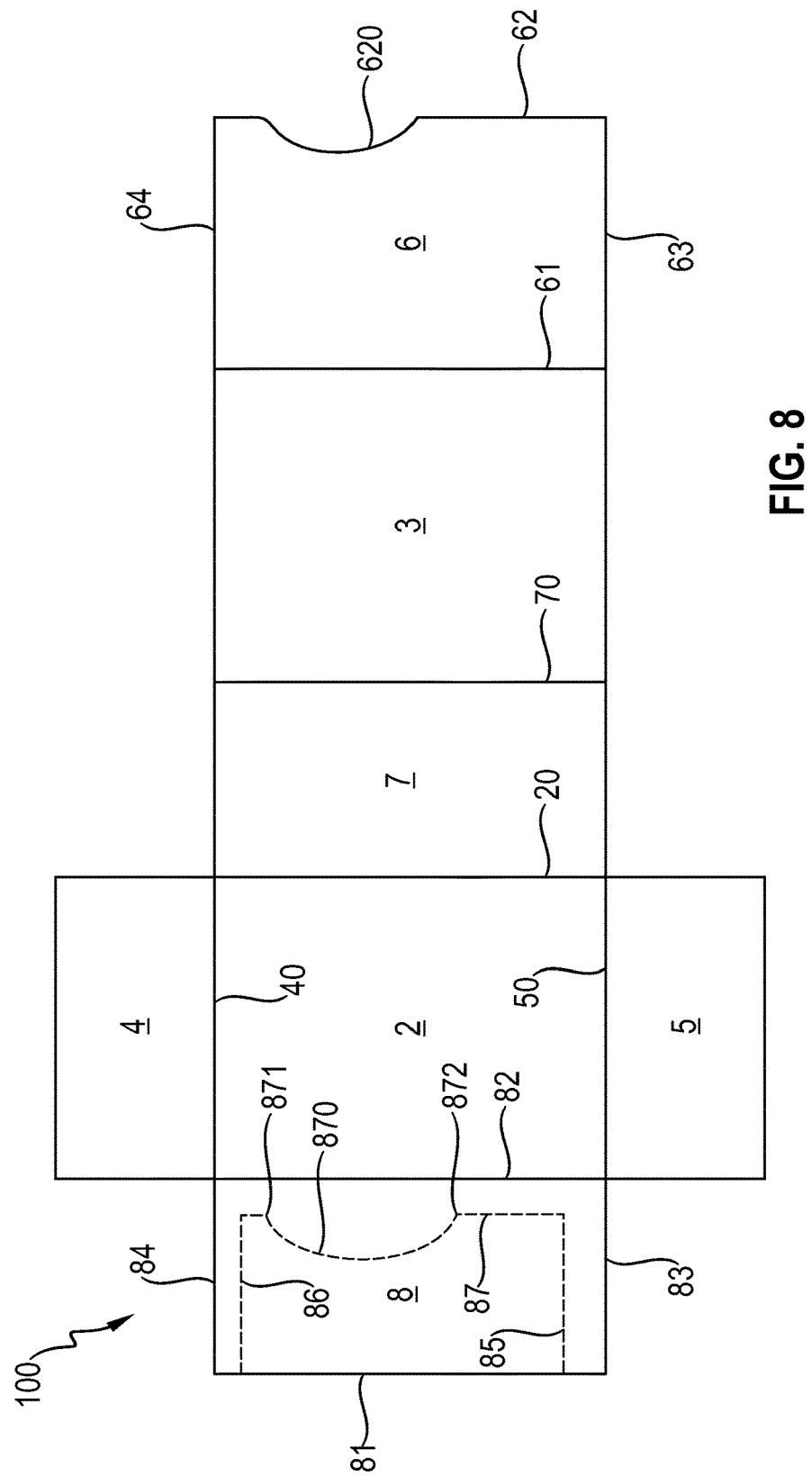
FIG. 8 is a front view of the blank having a substantially flat-shape.

A blank 100 is provided and has a substantially flat-shape. The blank 100 is able to be converted in the reclosable carton 1 having a substantially parallelepiped-shape. FIG. 8 shows a flexible package 120 within the scope of the invention.

When the blank 100 is converted in the reclosable carton 1, the blank 100 comprises a front wall 2, a rear wall 3, a first and second opposite side walls 4, 5, a top wall 8, a bottom wall 7 opposite to the top wall 8 and a lid 6.

As exemplary indicated in FIG. 8, the bottom wall 7 of the blank 100 is foldably connected to the rear wall 3 at a fold line of the bottom wall 70. The lid 6 of the blank 100 is foldably connected to the rear wall 3 at a fold line 61 of the lid 6 which is the hinge line 61 of the reclosable carton 1. The lid 6 of the blank 100 is opposite to the bottom wall 7 of the blank 100.

The front wall 2 of the blank 100 is opposite to the rear wall 3 with respect to the bottom wall 7 and is foldably connected to the bottom wall 7 at a fold line 20 of the front wall 2. The fold line 20 of the front wall 2 is parallel to the fold line 70 of the bottom wall 7.

The first side wall 4 of the blank 100 is foldably connected to the front wall 2 at a fold line 40 of the first side wall 4. The second side wall 5 of the blank 100 is opposite to the first side wall 4 with respect to the front wall 2 and is foldably connected to the front wall 2 at a fold line 50 of the second side wall 5. The fold line 40 of the first side wall 4 is parallel to the fold line 50 of the second side wall 5.

The top wall 8 of the blank 100 is foldably connected to the front wall 2 at a fold line 82 of the top wall 8 which coincides with the second transversal edge 82 of the top wall 8. The fold line 82 of the top wall 8 is parallel to the fold line 20 of the front wall 2 and perpendicular to the fold lines 40, 50 of the respective first and second side walls 4, 5.

The lid 6 of the blank 100 has first and second opposite transversal edges 61, 62 and first and second opposite longitudinal edges 63, 64. The first transversal edge 61 of the lid 6 coincides with the fold line 61 of the lid 6, which connects the lid 6 to the rear wall 3. At least a portion of the second transversal edge 62 of the lid 6 is a curve 620. The second transversal edge 62 of the lid 6 may comprise a curve 620.

The top wall 8 comprises first and second opposite transversal edges 81, 82 and first and second opposite longitudinal edges 83, 84. The first transversal edge 81 of the top wall 8 is substantially parallel to the fold line 82 of the top wall 2. The top wall 8 comprises first, second and third lines of weakness 85, 86, 87. The first and second lines of weakness 85, 86 extend, preferably perpendicularly, from the first transversal edge 81 of the top wall 8. The third line of weakness 87 converges with the first and second lines of weakness 85, 86. The first line of weakness 85 extends transversally inboard from the first longitudinal edge 83 of the top wall 8. The second line of weakness 86 extends transversally inboard from the second longitudinal edge 84 of the top wall 8. The third line of weakness 87 extends longitudinally inboard from the second transversal edge 82 of the top wall 8. At least a portion of the third line of weakness 87 of the top wall 8 is a curve 870. The third line of weakness 87 of the top wall 8 may comprise a curve 870.

As shown in FIG. 8, the curve 870 of the third line of weakness 87 extends from a first location 871 to a second location 872 of the third line of weakness 87. When the blank 100 is converted into the reclosable carton 1, the curve 620 of the second transversal edge 62 of the lid 6 and the curve 870 of the third line of weakness 87 of the top wall 8 are offset with each other at least between the first and the second location 871, 872 of the third line of weakness 87 by an offset distance θ. The offset distance θ between the curve 620 of the second transversal edge 62 of the lid 6 and the curve 870 of the third line of weakness 87 of the top wall 8 varies and reaches a maximum between the first and second location 871, 872 of the third line of weakness 87. The second transversal edge 62 of the lid 6 is then able to slip below the third line of weakness 87 of the top wall 8 such that the carton 1 is reclosable.

When the blank 100 is converted into the reclosable carton 1, the offset distance θ between the curve 620 of the second transversal edge 62 of the lid 6 and the curve 870 of the third line of weakness 87 of the top wall 8 is from about 3 mm to about 50 mm, or from about 3 mm to about 20 mm or from about 3 mm to about 10 mm when the blank 100 is converted into the reclosable carton 1, for all types of reclosable cartons.

Figure 9:
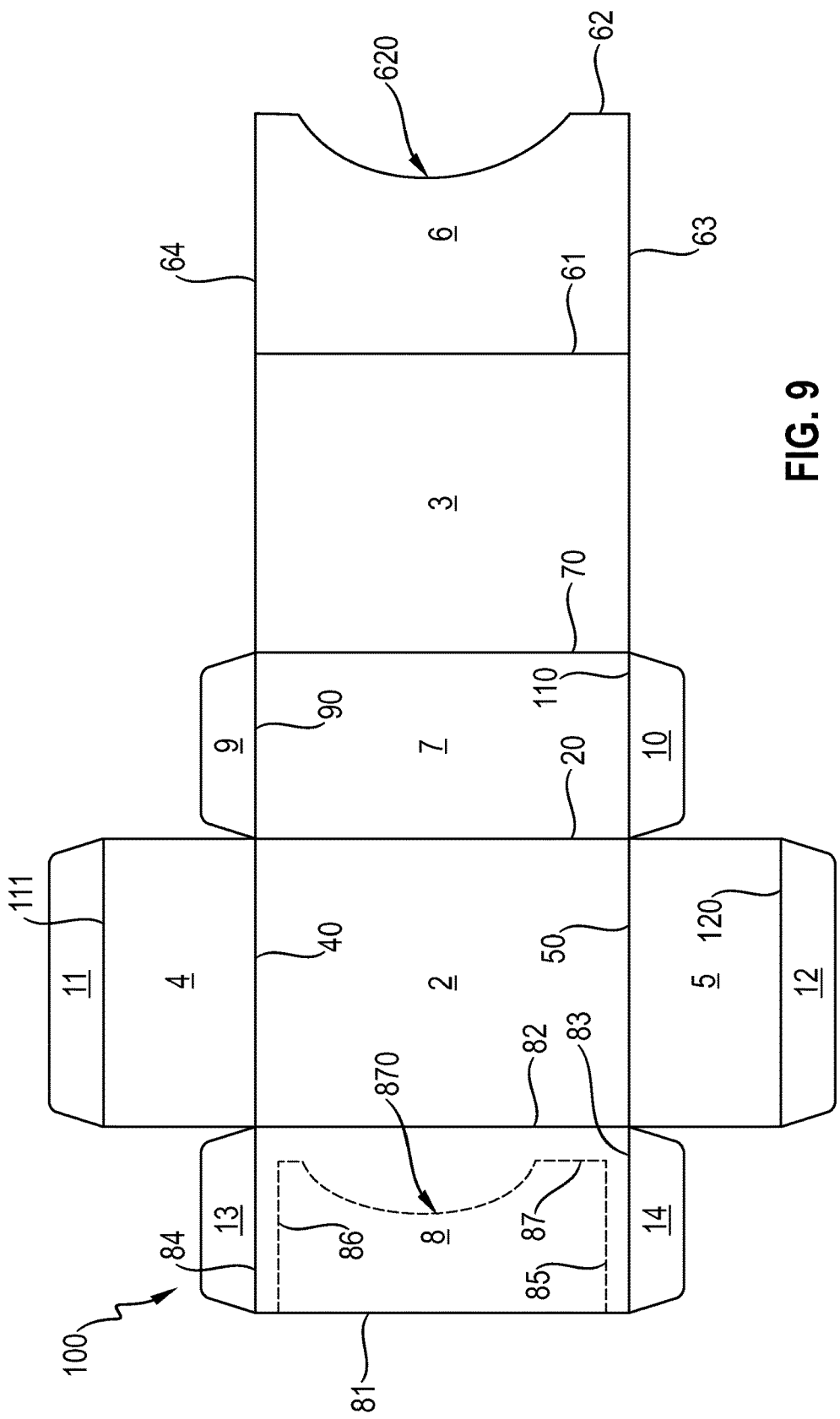
FIG. 9 is a front view of the blank having a substantially flat-shape and a plurality of flaps.

Furthermore, as indicated in FIG. 9, the blank 100 may comprise a first and second bottom flaps 9, 10, a first and second side flaps 11, 12 and a first and second top flaps 13, 14. The first bottom flap 9 of the blank 100 may be foldably connected to the bottom wall 7 at a fold line 90 of the first bottom flap 9. The fold line 90 of the first bottom flap 9 is perpendicular to the fold line 70 of the bottom wall 7. The first bottom flap 9 may be opposite to the second bottom flap 10. The second bottom flap 10 of the blank 100 may be foldably connected to the bottom wall 7 at a fold line 110 of the second bottom flap 10. The fold line 110 of the second bottom flap 10 is perpendicular to the fold line 70 of the bottom wall 7.

The first side flap 11 of the blank 100 may be foldably connected to the first side wall 4 at a fold line 111 of the first side flap 11. The fold line 111 of the first side flap 11 is parallel to the fold line 40 of the first side wall 4. The second side flap 12 of the blank 100 may be foldably connected to the second side wall 5 at a fold line 120 of the second side flap 12. The fold line 120 of the second side flap 12 is parallel to the fold line 50 of the second side wall 5.

The first top flap 13 of the blank 100 may be foldably connected to the top wall 8 at a fold line 84. The fold line 84 of the first top flap 13 is perpendicular to the fold line 82 of the top wall 8. The second top flap 14 of the blank 100 may be foldably connected to the top wall 8 at a fold line 83 of the second top flap 14. The fold line 83 of the second top flap 14 is perpendicular to the fold line 82 of the top wall 8.

The first and second bottom flaps 9, 10, the first and second side flaps 11, 12 and the first and second top flaps 13, 14 of the blank 100 are placed in the interior of the reclosable carton 1 and are likely not be visible from the exterior of the reclosable carton 1 once it has been erected. The first and second bottom flaps 9, 10 may be folded up and glued or stapled to the respective first and side wall 4, 5 of the reclosable carton 1. The first and second side flaps 11, 12 may be folded up and glued or stapled to the rear wall of the reclosable carton 1. The first and second top flaps 13, 14 of the blank 100 may be folded up and glued or stapled to the respective first and side walls 4, 5 of the reclosable carton 1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A reclosable carton for accommodating a plurality of disposable absorbent articles, the carton comprising:
    a wall defined by opposing first and second longitudinal edges and opposing first and second transversal edges, the wall comprising a frame having a first portion extending inwardly from the first longitudinal edge, a second portion extending inwardly from the second longitudinal edge and a third portion extending inwardly from the second transversal edge, the third portion having an inwardmost edge with an inwardly projecting portion defined by a first curve; and
    a lid extending inwardly from a proximal portion at a hinge line proximate the first transversal edge, the lid having opposing longitudinal lid edges and a distal transversal lid edge, the transversal lid edge having a recessing portion defined by a second curve;
    wherein the third portion, the inwardly projecting portion, the lid, and the recessing portion are sized and configured to permit closing of the lid and engagement of the recessing portion and the projecting portion in a configuration wherein the lid overlays the first and second portions of the frame and the recessing portion underlies the projecting portion.

2. A reclosable carton for accommodating a plurality of disposable absorbent articles, the carton comprising:
    a. a top wall comprising:
        i. opposing first and second longitudinal edges;
        ii. opposing first and second transversal edges;
        iii. first and second lines of weakness inboard of said opposing first and second longitudinal edges, respectively;
        iv. a third line of weakness inboard of said second transversal edge;
        v. a frame delimited by the first and second longitudinal edges, portions of the first transversal edge, the second transversal edge, and the first, second and third lines of weakness;
        vi. a curve along said third line of weakness defining an inward projection of the frame toward the first transversal edge;
        vii. wherein portions of the frame along the first and second longitudinal edges do not connect so as to maintain an opening for access to an interior of the carton;
    b. a lid which overlays portions of the frame along both the first and second longitudinal edges before the carton is opened initially and when the carton is reclosed; and wherein a distal portion of the lid resides underneath the projection when the carton is reclosed.

3. The carton of claim 2, wherein the lid is pivotally affixed to the first transversal edge.

* * * * *